United States Patent [19]

Kupperman et al.

[11] 4,361,044
[45] Nov. 30, 1982

[54] SCANNING ULTRASONIC PROBE

[75] Inventors: David S. Kupperman, Oak Park; Karl J. Reimann, Lisle, both of Ill.

[73] Assignee: The United States of America as represented by the United States Department of Energy, Washington, D.C.

[21] Appl. No.: 214,802

[22] Filed: Dec. 9, 1980

[51] Int. Cl.³ ............................................. G01N 29/04
[52] U.S. Cl. ...................................... 73/623; 73/642; 73/1 DV
[58] Field of Search ................. 73/622, 623, 628, 637, 73/638, 640, 1 DV, 620, 642

[56] References Cited

U.S. PATENT DOCUMENTS

| | | | |
|---|---|---|---|
| 2,825,044 | 2/1958 | Peterson | 73/623 |
| 4,022,055 | 5/1977 | Flournoy et al. | 73/622 |
| 4,084,582 | 4/1978 | Nigam | 73/642 |
| 4,212,207 | 7/1980 | Conradi | 73/623 |

OTHER PUBLICATIONS

K. J. Longua et al., "Equipment for Nondestructive Testing of 2¼ Cr, 1 Mo Duplex LMFBR Steam Generator Tubing", *Materials Evaluation*, pp. 54–59, Oct. 1977.

H. H. Neely et al., "Boreside Rotating Ultrasonic Tester for Wastage Determination of LMFBR-Type Steam Generator Tubes", *American Society for Nondestructive Testing*, pp. 275–278, 1979.

K. V. Cook et al., "Dev. of Ultrasonic Methods for Bore-Side Inspection of B. and W. Steam Gen. Tube-To-Tubesheet Welds", pp. 1–27, Jul. 1980.

*Primary Examiner*—Stephen A. Kreitman
*Attorney, Agent, or Firm*—Paul A. Gottlieb; Richard G. Besha; James E. Denny

[57] ABSTRACT

The invention is an ultrasonic testing device for rapid and complete examination of the test specimen, and is particularly well suited for evaluation of tubular test geometries. A variety of defect categories may be detected and analyzed at one time and their positions accurately located in a single pass down the test specimen.

13 Claims, 4 Drawing Figures

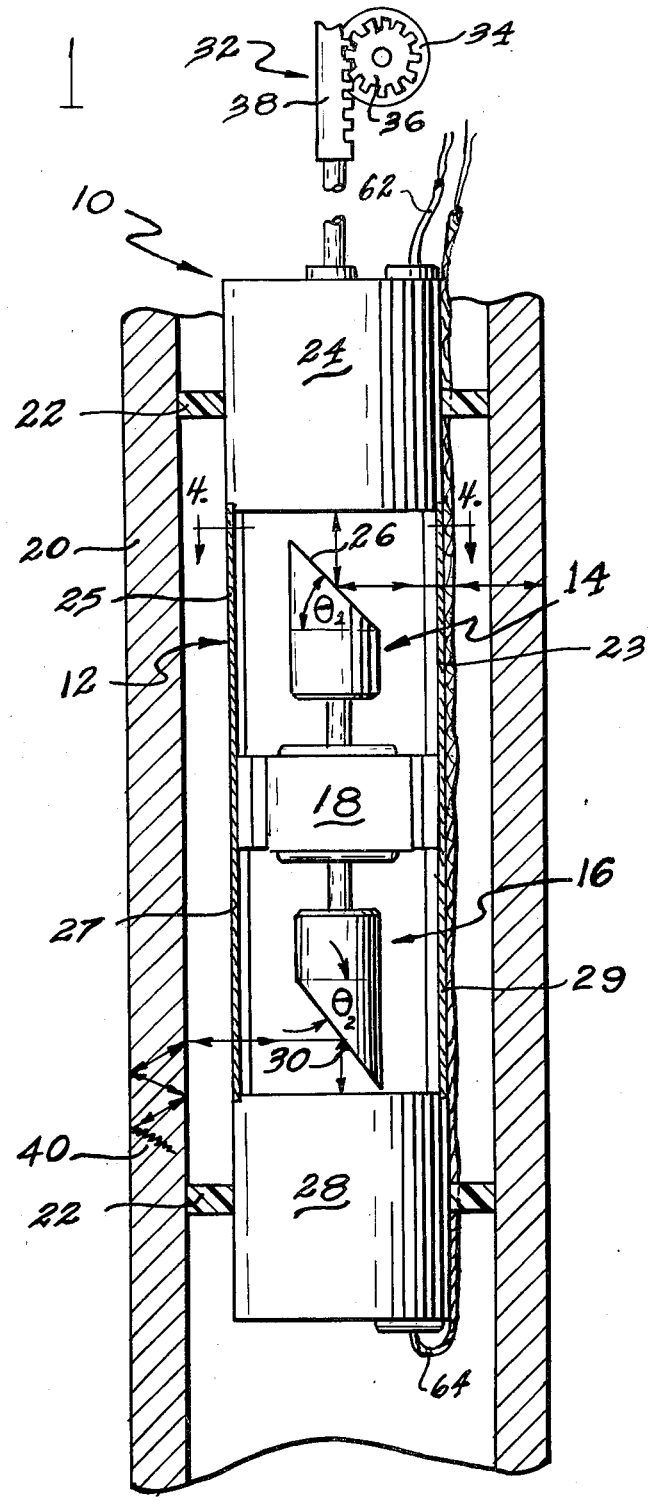

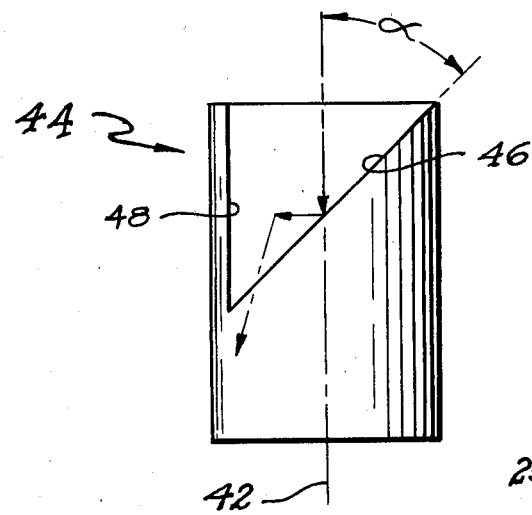
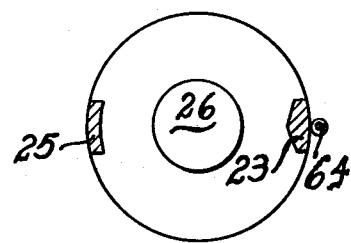
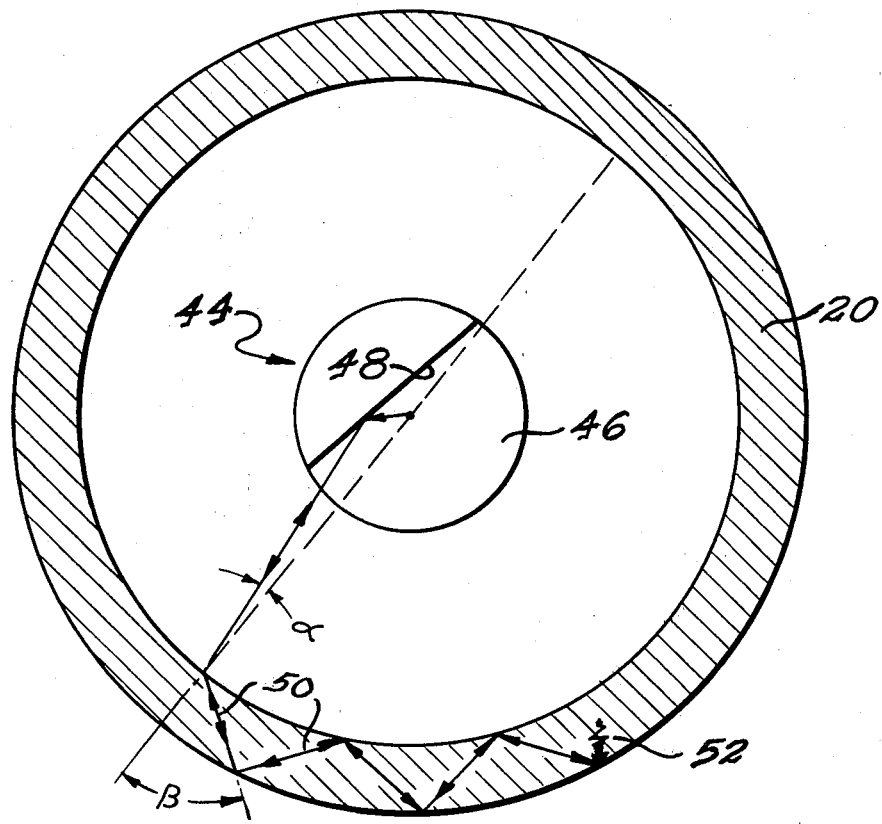

SCANNING ULTRASONIC PROBE

CONTRACTUAL ORIGIN OF THE INVENTION

The U.S. Government has rights in this invention pursuant to Contract No. W-31-109-ENG-38 between the U.S. Department of Energy and Argonne National Laboratory.

BACKGROUND OF THE INVENTION

The reliable use of ceramics as structural components requires effective means for detection of defects in the material in order to evaluate the possibility of material failure. For example, the lifetime of ceramic components can be affected by cracks, porosity, and foreign inclusions. Furthermore, many fractures originate near the surface, indicating that surface defects such as cracks or small cavities can be an important source of such failures. The critical size of cracks or pores which may lead to fracture can be relatively small in ceramic parts as compared with metal parts. A variety of nondestructive evaluation methods are used to probe for the presence of small defects in materials including microfocus x-radiography, microwave nondestructive evaluation, acoustic surface wave testing, photo-acoustic microscopy, acoustic emission detection, and high frequency ultrasonic testing.

Examination of tubing, in particular, can be a demanding task due to the possibility of extensive lengths to be examined and the difficulty of examining inner-tubular areas which have poor accessibility. Currently, tubular members are examined ultrasonically in one of three ways:

(1) by the passing of an ultrasonic transducer through the tube and detecting and analyzing the transmitted or reflected ultrasonic signals (see K. J. Longua, G. K. Whitman, and J. T. McElroy, Matl. Eval., 54 (1977);

(2) by the mounting of the tubular member on a lathe or related device, translating and rotating the tubing about a fixed transducer, and detecting and analyzing the signals from the transducer (see K. V. Cook and R. A. Cunningham, Jr., ORNL/TM-7373 (1980); or (3) by the driving of a turbine with a flowing stream of water, with the turbine containing an ultrasonic transmitter and receiver (see H. H. Neely and H. L. Renger, Am. Soc. Non-Destructive Testing, National Fall Conference, p. 275, St. Louis, Mo., Oct. 1979).

The first method is extremely tedious and time consuming to carry out since a large set of linear scans is required to examine the entire tubing. In the second method, the movement of the tubular member is inconvenient at best and at worst can be impossible if the tubing is fixed in place. In the last method it is possible to carry out a circumferential and linear scan without rotating and translating the entire probe package, but the circumferential scan is dependent on fluid flow turning a turbine which contains the probe. Dependence upon fluid flow dictates sharp limitations on the probe capabilities, such as scan speed and even the feasibility of using such a scheme if the test conditions make it impossible to induce the flow of fluid through the tube to be examined.

It is therefore an object of the invention to provide a device for the complete ultrasonic scanning examination for defects in test materials.

It is also an object of the invention to provide a device of integral structure having one or more rotating and scanning ultrasonic mirrors which permit rapid, complete ultrasonic examinations for defects in tubular materials.

It is a further object of the invention to provide an ultrasonic probe device having two motor driven rotating and scanning ultrasonic mirrors which simultaneously analyze for circumferential, longitudinal, or transverse defects from within a tubular material.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The invention provides a device for rapid and thorough non-destructive ultrasonic testing for defects from a position within tubular materials. The device is integral in construction with at least one fixed ultrasonic transducer, at least one rotatable mirror, and a fixed drive motor for the mirrors. This particular package also includes for each mirror, at least one post which acts to reflect ultrasonic waves and establishes an intrinsic angular reference position for the rotational scan. Various types of mirrors may be used to generate ultrasonic waves in the test material to probe for longitudinal, transverse, and circumferential defects.

BRIEF DESCRIPTION OF THE DRAWINGS

FIG. 1 shows the ultrasonic probe having a first and second mirror,

FIG. 2 shows a mirror for creating circumferential ultrasonic shear waves, and

FIG. 3 shows the operation of the circumferential mirror in creating shear waves in a tubular material.

FIG. 4 shows a cross section along line 4—4 of FIG. 1.

DETAILED DESCRIPTION OF THE PREFERRED EMBODIMENT

The embodiment shown in FIG. 1 is one of the preferred configurations for the invention. The boreside ultrasonic probe assembly 10 shown in FIG. 1 is capable of performing an examination for transverse, longitudinal, or circumferential defects in one pass down the length of the tubular object to be examined. For example, this single pass scan ability may be accomplished by one of the rotating mirror assemblies scanning the tube for longitudinal inhomogeneities and the other assembly scanning for transverse, or circumferential defects. A different version of FIG. 1, having lesser capabilities, would include only one mirror to scan either for transverse, longitudinal, or circumferential defects in one pass. By external control of the angle of sweep of the mirror (by a programmable power supply) a portion of a tube or an incomplete section of a shape may also be examined. This would enable non-circular tube cross sections, such as square or rectangular, and shapes other than completely enclosed tubes to be analyzed.

The ultrasonic probe assembly 10 is supported by casement 12 which contains a first assembly 14, second assembly 16, and mirror drive 18. Casement 12 is centered within tube 20 by teflon spacers 22 which allow low-friction movement of probe 10 within the tube to be examined. First assembly 14 includes a first transducer assembly 24 and first mirror 26, and second assembly 16 includes second transducer assembly 28 and second mirror 30. As shown in FIG. 1, casement 12 is open as much as possible circumferentially about first mirror 26 and second mirror 30 in order to allow as complete an ultrasonic circumferential scan as is possible. To obtain this circumferentially open geometry, the only support between the mirror drive 18 and transducer assemblies 24 and 28 are slender support members. These support members are two in number for both first assembly 14 and for second assembly 16. The support members for first assembly 14 are first and second calibration posts 23 and 25 and are shown in cross section in FIG. 4. The support members for second assembly 16 are fourth calibration posts 27 and 29 which typically are the same as posts 23 and 25, respectively. These posts serve not only as support members but also as a means for calibrating the angular position of detected ultrasonic waves, and this will be discussed later.

Assembly 10 may be scanned linearly along the length of tube 20 by a drive means such as linear step drive assembly 32. In FIG. 1, assembly 32 includes a motor drive 34, gear assembly 36, and step scan drive arm 38 connected to casement 12. This drive assembly 32 may be run at a constant slow drive speed, but preferably is run in small incremental steps. As is well known in the art, an electronic signal may be generated which is proportional to the length of drive into tube 20 by drive assembly 32 and may be outputted to a data analysis system, thereby establishing a linear position of the probe 10 along the tube length.

In order to carry out a circumferential, as well as lengthwise, ultrasonic beam scan of tube 20, mirrors 26 and 30 are rotated by mirror drive 18. Mirror drive 18 may be a single motor which drives both the first mirror 26 and second mirror 30, or two independent motor drives may be utilized. Independent motor drives may be necessary in situations which demand more flexibility in examining procedures, for example, during detailed inspection of a test material with a preferred high density of transverse or longitudinal type defects. It is also possible to use a magnetic motor drive coupling rather than direct drive, which enables a better seal to be established for the drive shaft, thereby prolonging the life of the drive means in a corrosive coupling medium.

It is also possible to create different ultrasonic modes in the tube 20 by changing the angle of incidence of the ultrasonic beam upon the inside of the tube walls. This may be accomplished by allowing removal and replacement of mirrors 26 and 30 or by providing a tilt mechanism (such as a goniometer dove-tail gear mount which is able to rock the mirrors about an arc) as part of mirror drive 18. By use of the goniometer type mount, the center of the mirror plane remains centered on the mirror drive axis 42, thereby avoiding variations in the angle of inclination of the mirror surface to the ultrasonic beam as the mirror rotates.

A longitudinal acoustic mode with particular sensitivity for internal tube wall delaminations or thin spots in the tube wall is obtained in the wall of tube 20 by emitting an acoustic wave from the ultrasonic mirror 26 such that the acoustic wave is perpendicular to the tube wall to be inspected. This requires the angle of the mirror $\theta_1$ in FIG. 1 to be approximately 45° for a longitudinal wave mirror. The ultrasonic wave is then re-flected back to mirror 26 and is reflected to assembly 24 which detects the sound wave.

In order to examine the tubular test piece along the tube length, an axial shear mode must be created in the tube wall. From Snell's Law, $$\sin \alpha / V_\alpha = \sin \beta / V_\beta$$

where $\alpha$ = angle of the acoustic waves with respect to a normal to the tube wall at the point of impact, $V_\alpha$ is the sound velocity in the fluid in which the tube 20 is immersed, $\beta$ is the angle of the converted mode with respect to the normal, and $V_\beta$ in the velocity in the tube 20. In FIG. 1 with water as the coupling medium and a ceramic tube undergoing a test, the angle $\theta_2$ must be approximately 41° in order to propagate a wave down the length of the ceramic tube. On encountering a defect 40, the axial shear wave is reflected back along its path of propagation, exits from the wall of tube 20, is reflected by the ultrasonic wave mirror 30, and is detected by the transducer assembly 28.

Circumferential shear waves which travel around the circumference of the tube wall without propagating down the length of the tube may be generated by means of circumferential mirror 44 shown in FIG. 2. Mirror 44 includes two intersecting mirror surfaces: (1) a first surface 46 at an angle $\alpha$ (typically near 45°) to the mirror drive axis 42 and (2) a second surface 48 nominally parallel to mirror drive axis 42. This configuration of mirror surfaces 46 and 48 result in a translational offset of the ultrasonic beam as shown in FIG. 3. The ultrasonic beam from the transducer initially strikes first surface 46, is reflected to second surface 48 which reflects the beam onto the inside wall of tube 20. As known in the art, mode conversion within this geometry results in the creation of a shear wave 50. This shear wave propagates by a series of reflections until the wave has encountered defect 52, whereupon a portion of the wave intensity is reflected back along the path of propagation, reflected by one of the ultrasonic mirrors detected by a transducer assembly, and evaluated by an appropriate data analysis system. Consequently, a variety of ultrasonic modes may be created through use of the appropriate mirror and resultant ultrasonic mode conversion of the acoustic waves incident upon the wall.

Ultrasonic mirrors 26 and 30 may be made of any polished metal or any material which efficiently reflects ultrasonic waves of interest. Corrosion resistant stainless steels are often used due to their durability in corrosive environments (tubes for examination or other geometries are typically immersed in water). For metallic tubes, the maximum frequency will be approximately 20 megahertz and for plastic tubes about 10 megahertz. For testing ceramic tubes, frequencies up to 35 megahertz may be used in typical coupling media such as water, oil, or alcohol.

In order to affix an angular position to the detected acoustic signals, first and second angle calibration posts 23 and 25, respectively, reflect ultrasonic waves which are detected by first transducer assembly 24. The geometry of posts 23 and 25 are usually different in order to distinguish the two angular positions. For example, a flat face may be used on one and a shallow wedge on the other (see FIG. 4). This difference is post shape then enables one to establish unambiguously the angular position in the tube wall of various detected signals by means of the signals from posts 23 and 25 in relation to the detected ultrasonic signals from the defects. Similarly, for second assembly 16, the calibration posts 27 and 29, respectively, enable the angular position of various signals to be established by internal standardization. The resolution of the probe is dictated by the beam size, which is typically of the order of three millimeters in diameter, with the ultimate resolution for individual defects in the vicinity of 100 micrometers.

The reflected ultrasonic signals detected by first transducer assembly 24 and second transducer assembly 28 are outputted via first electronic cabling 62 and second electronic cabling 64, respectively. Electronic analysis is performed by utilizing the following: the detected output signals, the reflected ultrasonic signals from the angular calibration posts 23, 25, 27, and 29 and the linear position signal from linear scan drive assembly 32. Data analysis may then be performed and the nature of a defect and its precise spatial position with respect to the end of tube 20 may be ascertained. The data analysis system may also include a microprocessor control system, which permits automated examination of the test piece during automatic data accumulation.

The embodiment of the invention in which an exclusive property or privilege is claimed are defined as follows:

1. An ultrasonic probe for examining a test piece comprising: at least one transducer assembly capable of producing an ultrasonic beam, at least one circumferential wave mirror aligned with said transducer assembly such that said mirror is capable of reflecting the ultrasonic beam from said transducer assembly toward a test piece and capable of directing a reflected ultrasonic wave from the test piece to said transducer assembly for detection, said mirror having at least two surfaces which are capable of offsetting the final point of emergence from said mirror of the incident ultrasonic beam from the transducer to a point removed from the optical axis of said transducer assembly, thereby enabling a circumferential shear wave to be produced in the test piece; and a mirror drive means coupled to said mirror.

2. An ultrasonic probe for examining a test piece comprising, a first ultrasonic assembly, a second ultrasonic assembly, said first ultrasonic assembly including a first ultrasonic transducer, a first ultrasonic mirror capable of reflecting the ultrasonic beam from said first transducer onto the test piece to create a first acoustic wave in the test piece and said first mirror capable of directing a reflected ultrasonic wave from the test piece to said first transducer for detection, and at least one first angle calibration post interposed between said first mirror and the test piece, said second ultrasonic assembly including a second ultrasonic transducer, a second ultrasonic mirror capable of reflecting the ultrasonic beam from said second transducer onto the test piece to create a second acoustic wave in the test piece and said mirror capable of directing a reflected ultrasonic wave from the test piece to said second transducer for detection, at least one second angle calibration post interposed between said second mirror and the test piece, said second ultrasonic assembly capable of generating different ultrasonic signals than said first ultrasonic assembly, a mirror drive means rotatably coupled both to said first ultrasonic mirror and to said second ultrasonic mirror, and a linear drive means for moving said ultrasonic probe from position to position along the test piece.

3. The device of claim 2 wherein said second ultrasonic signal is capable of analyzing different defects in the test piece.

4. The device of claim 2 wherein said first ultrasonic mirror is a longitudinal wave mirror and said second ultrasonic mirror is an axial shear wave mirror.

5. The device of claim 2 wherein said first ultrasonic mirror is a circumferential wave mirror and said second ultrasonic mirror is a longitudinal wave mirror.

6. The device of claim 2 wherein said first ultrasonic mirror is a circumferential wave mirror and said second ultrasonic sonic mirror is an axial shear wave mirror.

7. The device of claim 2 further comprising a third ultrasonic assembly, said third ultrasonic assembly including a third ultrasonic transducer, a third ultrasonic mirror capable of reflecting the ultrasonic beam from said third transducer onto the test piece to create a third acoustic wave in the test piece and said third mirror capable of directing a reflected ultrasonic wave from the test piece to said third transducer for detection.

8. The device of claim 7 wherein said first ultrasonic mirror is a longitudinal wave mirror, said second ultrasonic mirror is an axial shear wave mirror and said third ultrasonic mirror is a circumferential wave mirror.

9. An ultrasonic probe for examining a test piece comprising: at least one transducer assembly capable of producing an ultrasonic beam, at least one mirror aligned with said transducer assembly such that said mirror is capable of reflecting the ultrasonic beam from said transducer assembly toward a test piece and capable of directing a reflected ultrasonic wave from the test piece to said transducer assembly for detection, a first calibration post interposed between said mirror and the test piece, a second calibration post interposed between said mirror and the test piece, and a mirror drive means coupled to said ultrasonic mirror, wherein the shape of said first calibration post is different from the shape of said second calibration post.

10. The device of claim 9 wherein said ultrasonic mirror further includes a tilting means coupling said ultrasonic mirror to said mirror drive means.

11. The device of claim 10 wherein said tilting means is a goniometer.

12. The device of claim 11 wherein said mirror drive means further includes a mirror drive control means for programming the magnitude of the angular sweep and sweep speed of said ultrasonic mirror.

13. The device of claim 12 further including a linear drive means coupled to said probe whereby said probe may be moved from position to position along the test piece.

* * * * *